Jan. 31, 1961 H. C. SWIM ET AL Plant Pat. 2,018
ROSE PLANT
Filed April 11, 1960
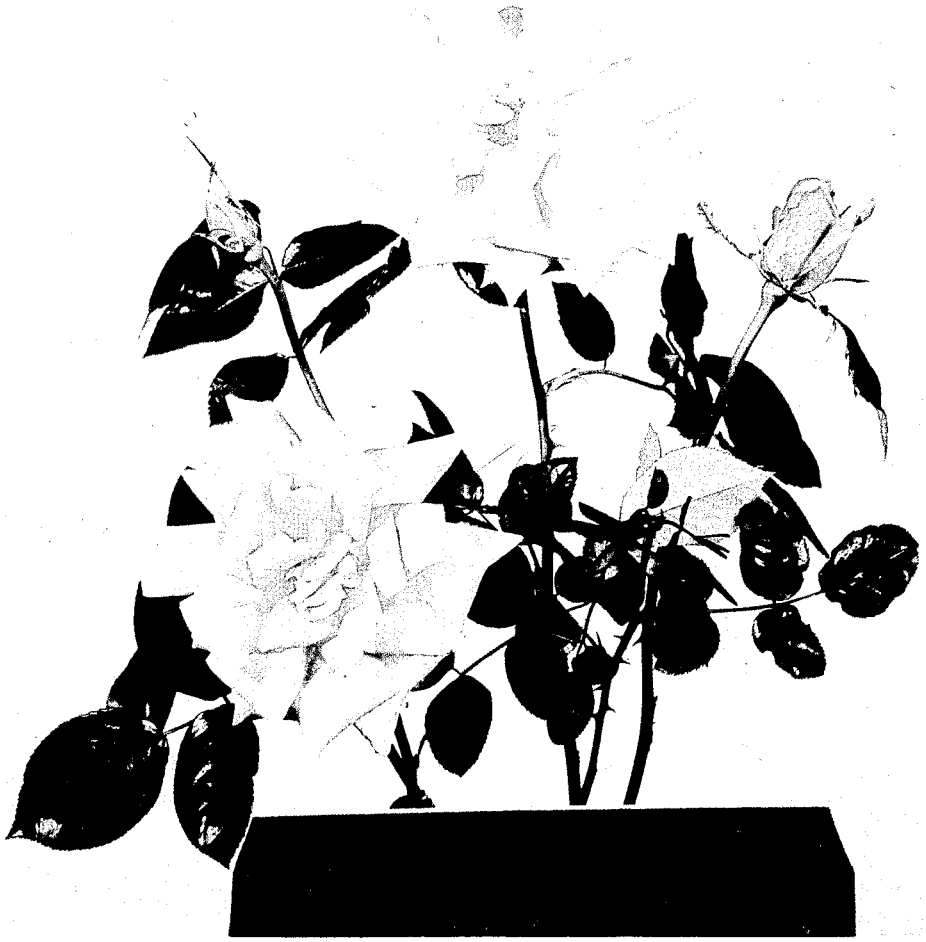
INVENTOR
H. C. Swim and O. L. Weeks
BY Robb & Robb
ATTORNEYS United States Patent Office Plant Pat. 2,018

Patented Jan. 31, 1961

2,018

ROSE PLANT

Herbert C. Swim, Ontario, and O. L. Weeks, Chino, Calif., assignors to The Conard-Pyle Company, West Grove, Pa., a corporation of Pennsylvania Filed Apr. 11, 1960, Ser. No. 21,572

1 Claim. (Cl. 47—61)

The present invention relates to a new and distinct variety of rose plant of the hybrid tea class, which was originated by us by crossing the variety "Charlotte Armstrong" (Plant Patent No. 455) with the variety "Signora" (Plant Patent No. 201).

As the result of this breeding, we have created a new rose variety which is endowed with the following unique and desirable combination of characteristics which are outstanding therein and which distinguish it from its parents, as well as from all other varieties of which we are aware:

(1) Vigorous and productive plant habits;

(2) A neat and compact plant form, with many erect branches which are well-placed and well-proportioned;

(3) Attractive foliage of large size and abundance, which give the plant a well-clothed appearance;

(4) A relative scarcity of prickles on the flower stems, as compared with most varieties now in commerce;

(5) Graceful proportions of the bud in relation to the number of flower petals; and (6) A distinctive and variable blend of pink and yellow flower color pigments, but generally ranging in the colors popularly referred to as salmon, orange and pink, as well as combinations of these colors, thus resulting in an unusual color tonality that is definitely different from that found in any other rose now in commerce.

In comparison with its seed parent, "Charlotte Armstrong," our new rose variety is more upright in its habit of growth; has glossy foliage in contrast to the non-glossy foliage of this parent; has fewer prickles than its parent; produces flowers of salmon and orange color tones which are quite different from the pink and red color tones of the flowers of "Charlotte Armstrong;" and the flowers have a much stronger fragrance than those of this parent.

As compared with its pollen parent, "Signora," the new variety is more productive and has a substantially bushier plant habit; the individual flower stems are substantially shorter than those of this parent; the flower buds are substantially larger in proportion to their width than those of this parent; and the flowers of the new variety are dominated by pink and orange colors, while those of this parent are dominated by red and yellow colors and combinations thereof.

Asexual reproduction of our new rose variety by budding, as performed at Chino, California, shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with the Nickerson Color Fan, published by Munsell Color Company, Inc., of Baltimore, Maryland, except where general color terms of ordinary dictionary significance are obvious:

Type: Hardy; bush; outdoor; seedling; for cut flowers and for garden decoration.

Class: Hybrid tea.

Breeding: Seedling.

*Seed parent.*—"Charlotte Armstrong."

*Pollen parent.*—"Signora."

Propagation: Holds its distinguishing characteristics through succeeding propagations by budding.

*Flower*

Locality where grown and observed: Chino, California.

Flowers borne: Singly and sometimes 2 or more to stem; on strong stems of medium length.

Quantity of bloom: Free, outdoors.

Continuity: Continuous during growing season.

Fragrance: Strong. Nature—tea.

Bud:

*Peduncle.*—Long; medium caliper; erect; with numerous small prickle-like glands, particularly on lower half.

*Before calyx breaks.*—Size—medium. Form—long; pointed; with a conspicuous neck; with foliaceous appendages on the surface of the bud; with slender foliaceous parts extending beyond the tip of the bud equal to its length. Color—near Strong Yellow Green, Plate 7.5GY6/8.

*As calyx breaks.*—Color—upper portion near Strong Yellowish Pink, Plate 10R7/9, with lower portion near Brilliant Yellow, Plate 2.5Y9/9, these colors blending in central portion.

*As first petal opens.*—Size—large. Form—long; pointed. Color: outside — generally between Strong Red, Plate 2.5R5/12 and Vivid Red, Plate 5R5/13, except near base where a blend of this latter color and a yellow shade gradually gives way to Vivid Yellow, Plate 5Y8/12, at point of attachment; inside—Vivid Red, Plate 5R5/13 and variously overlaid, mottled and/or veined with Strong Red, Plate 5R4/12, except at base where the former color gives way to Vivid Yellow, Plate 5Y8/12.

*Opening.*—Opens up well; is not retarded by cold, hot, wet or dry weather.

Bloom:

*Size (when fully opened).*—Large; from 4¼ inches to 4¾ inches.

*Petalage.*—Double; from 25 to 35 petals, with a few petaloids; arranged more or less regularly.

*Form.*—High-centered at first, but becoming open; petals being at first loosely rolled outward, but later becoming more tightly rolled outward at maturity.

Petals:

*Texture.*—Medium thick; soft. Inside—satiny. Outside—satiny.

*Shape.*—Outside—broadly obovate, with apex acute. Intermediate—obovate, with apex acute. Inside—obovate-truncate, with apex acute.

This description of a newly opened flower was made from a rose grown in a greenhouse at Chino, California, during the month of December:

*Color.*—Outer petal: outside surface—near Deep Pink, Plate 2.5R6/11 over upper ½ of petal, but blending with Brilliant Yellow, Plate 5Y9/9, progressing toward base and becoming this latter color entirely ⅛ inch from point of attachment; inside surface—near Deep Pink, Plate 10RP6/12 over outer ½ of petal, but with veins distinctly marked with Vivid Red, Plate 5R5/13; the former color blends with some shade of bright yellow in the inner or lower ½ of petal to give a shade near Strong Reddish Orange, Plate 7.5R6/12, but becoming Brilliant Yellow, Plate 5Y9/9 one-eighth inch from point of attachment. Intermediate petal: outside surface—near Deep Pink, Plate 2.5R6/11 over upper ½ of petal, but blending with Brilliant Yellow, Plate 5Y9/9, progressing toward base and becoming this latter color entirely ⅛ inch from point of attachment; inside surface—near Deep Pink, Plate 2.5R6/11 over outer ½ of petal, blending with some shade of bright yellow progressing toward base and giving way to Brilliant Yellow, Plate 5Y9/9 in small area about point of attachment, with distinctive veining throughout upper surface, except in small area of Brilliant Yellow, Plate 5Y9/9 at base, said veins being near Strong Reddish Orange, Plate 7.5R6/12. Inner petal: outside surface—near Deep Yellowish Pink, Plate 5R6/11 over upper ½ of petal and near Strong Yellowish Pink, Plate 7.5R7/9 over lower ½, except for small area around point of attachment and irregular streak along midrib which starts at point of attachment with Brilliant Yellow, Plate 7.5Y9/8, but loses some intensity as it progresses toward apex of petal; inside surface—near Deep Pink, Plate 2.5R6/11 around outer margin of petal on the upper or outer ½, with center of petal heavily influenced by veining of Strong Red, Plate 2.5R5/12; lower ½ near Strong Reddish Orange, Plate 10R6/12, except at base where small area is Brilliant Yellow, Plate 5Y9/9.

This description was made from a rose that was open for three days in a greenhouse at Chino, California, during the month of December:

*Color.*—Outer petal: outside surface—upper ⅓ near Strong Purplish Pink, Plate 5RP7/9, with base Brilliant Greenish Yellow, Plate 7.5Y9/8; these colors blend as they overlap in their influence in that area ¼ inch from base to ½ inch from apex, with each color fading out at the limit opposite its origin; over the upper ¾ of the petal, a faint veining of Strong Purplish Pink, Plate 7.5RP7/10 is apparent; inside surface—Light Purplish Pink, Plate 2.5RP8/5 over upper ½, modified by numerous veins of Deep Purplish Pink Plate 7.5RP6/12; lower ½ is modified by undertone of yellow, becoming progressively more intense in hue as the base is approached, and becoming Brilliant Yellow, Plate 5Y9/9 about ¼ inch from base and continuing to point of attachment. Inner petal: outside surface—base near Brilliant Greenish Yellow, Plate 7.5Y9/8, beginning to blend with pink about ¼ inch from base and progressively diminishing in effect toward apex until all yellow influence is lost about ½ inch from apex and Strong Pink, Plate 10RP7/8 appears, with much of the blended area near Moderate Yellowish Pink, Plate 7.5R8/6; inside surface—upper ½ of petal near Deep Pink, Plate 10RP6/12, with base Brilliant Greenish Yellow, Plate 7.5Y9/8 to ¼ inch from point of attachment; remainder of petal near Moderate Yellowish Pink, Plate 10R8/6; in the area influenced or entirely occupied by pink tones, veining of near Deep Pink, Plate 10RP6/12 is noticeable.

*General color effect.*—Newly opened flower—dominant color at outer reaches of flower is Deep Pink, Plate 2.5R6/11, with heart of flower Brilliant Yellow, Plate 5Y9/9, and area in between is near Deep Yellowish Pink, Plate 5R6/11. 3-days open—outer part of flower is Deep Pink, Plate 10RP6/12, with heart of flower Brilliant Yellow, Plate 5Y9/9, with area between being a blend approaching Strong Yellowish Pink, Plate 7.5R7/9.

*Behavior.*—Drop off cleanly.

*Flower longevity.*—Cut roses grown in a greenhouse and kept at living room temperatures—3 days in December.

*Reproductive Organs*

Stamens: Many, arranged regularly about pistils.

Filaments: Medium length; most with anthers. Color—some near Strong Orange, Plate 2.5YR7/10; others near Strong Reddish Orange, Plate 10R6/12.

Anthers: From small to medium for this class of rose; all open at once more or less.

Pollen: Moderate. Color—Gold.

Pistils: Many.

Styles: Even; medium length; somewhat thin; bunched.

Stigma: Color—whitish yellow.

Ovaries: All enclosed in calyx.

Hips: Globular; usually without conspicuous neck; very smooth; walls thick and fleshy.

Sepals: Permanent; long; straight; often foliaceous.

Seeds: Few; large.

*Plant*

Foliage:

*Leaves.*—Compound of 5 to 7 leaflets; moderately abundant; large; moderately heavy and leathery; somewhat glossy.

*Leaflets.*—Shape—ovoid, with apex acute. Base—rounded. Margin—simply serrate.

*Color.*—Mature: upper surface—between moderate Olive Green, Plate 5GY4/3 and Grayish Olive Green, Plate 5GY3/2; under surface—between Light Yellowish Green, Plate 2.5G8/6 and very Light Bluish Green, Plate 2.5BG8/6. Young: upper surface—center of leaflets near Moderate Yellow Green, Plate 2.5GY5/5, faintly overlaid with Dark Red, Plate 5R3/7 and becoming the latter color at margins; under surface—veins, midrib and margin between Dark Red, Plate 5R3/7 and Moderate Reddish Brown, Plate 7.5R3/6, with some shade of green faintly showing through.

*Rachis (the supporting stem of the compound leaf).*—Upper side—grooved; hairy; with occasional glands. Under side—hairy; sometimes with one or two small prickles.

*Stipules.*—From short to medium length; medium width; with medium length points.

*Disease resistance.*—Better-than-average resistance to mildew in comparison with other varieties grown under comparable cultural conditions and climate at Chino, California.

Growth:

*Habit.*—Bushy; upright; much-branched.

*Growth.*—Very vigorous.

*Canes.*—Medium caliper.

*Main stems.*—Color—between Strong Yellowish Green, Plate 2.5GY6/8 and Moderate Yellow Green, Plate 2.5GY5/5. Large prickles—several; medium length; most slightly hooked downward; with short, broad base; color—brown. Small prickles—few; color—brown. Hairs—none.

*Branches.*—Color—between Strong Yellow Green, Plate 5GY6/8 and Moderate Yellow Green, Plate 5GY5/6. Large prickles—few; medium length; very slightly hooked downward; with short, broad base; color—brown. Small prickles—few; color—brown. Hairs—none.

*New shoots.*—Color—generally between Dark Red, Plate 5R3/7 and Deep Purplish Red, Plate 7.5RP3/9. Large prickles—few; medium length;

straight; with short, broad base; color—generally between Dark Red, Plate 5R3/7 and Deep Purplish Red, Plate 7.5RP3/9. Small prickles—few; color—reddish purple. Hairs—none.

We claim:

A new and distinct variety of rose plant of the hybrid tea class, substantially as herein shown and described, characterized particularly as to novelty by the unique combination of productive and vigorous plant habits, a heat and compact plant form, with many erect, well-placed and well-proportioned branches, attractive foliage of large size and an abundance thereof which gives the plant a well-clothed appearance, a relative scarcity of prickles on the flower stems, graceful proportions of the bud in relation to the number of flower petals, and a distinctive variable blend of pink and yellow flower color generally in the range of salmon, orange and pink and combinations thereof.

No references cited.